United States Patent
Lee et al.

(10) Patent No.: US 9,725,527 B2
(45) Date of Patent: Aug. 8, 2017

(54) MODIFIED CONJUGATED DIENE POLYMER, METHOD FOR PREPARING SAME, AND RUBBER COMPOSITION CONTAINING SAME

(71) Applicant: LG Chem, Ltd., Seoul (KR)

(72) Inventors: Ro-Mi Lee, Daejeon (KR); No-Ma Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/119,933

(22) PCT Filed: Oct. 22, 2015

(86) PCT No.: PCT/KR2015/011230
§ 371 (c)(1),
(2) Date: Aug. 18, 2016

(87) PCT Pub. No.: WO2016/076549
PCT Pub. Date: May 19, 2016

(65) Prior Publication Data
US 2017/0058055 A1      Mar. 2, 2017

(30) Foreign Application Priority Data

Nov. 13, 2014 (KR) .................. 10-2014-0158077
Oct. 6, 2015 (KR) .................. 10-2015-0140480

(51) Int. Cl.
| | | |
|---|---|---|
| C08C 19/44 | (2006.01) | |
| C08C 19/25 | (2006.01) | |
| C08K 5/544 | (2006.01) | |
| C08C 19/22 | (2006.01) | |
| C08K 3/36 | (2006.01) | |
| B60C 1/00 | (2006.01) | |

(52) U.S. Cl.
CPC ............ *C08C 19/44* (2013.01); *B60C 1/0016* (2013.01); *C08C 19/22* (2013.01); *C08C 19/25* (2013.01); *C08K 3/36* (2013.01); *C08K 5/544* (2013.01)

(58) Field of Classification Search
CPC .............................. C08C 19/22; C08C 19/25
USPC .................. 525/342, 374, 375, 382
See application file for complete search history.

(56) References Cited

U.S. PATENT DOCUMENTS

| | | | |
|---|---|---|---|
| 2009/0163668 A1 | 6/2009 | Yamada et al. | |
| 2009/0203843 A1 | 8/2009 | Fukuoka et al. | |
| 2011/0172344 A1 | 7/2011 | Yoshida et al. | |
| 2012/0277369 A1 | 11/2012 | Yoshida et al. | |
| 2013/0245192 A1 | 9/2013 | Tanaka et al. | |
| 2014/0309363 A1* | 10/2014 | Morita | B60C 1/0016 524/575 |
| 2014/0364560 A1* | 12/2014 | Backer | C08K 5/5442 524/575.5 |

FOREIGN PATENT DOCUMENTS

| | | |
|---|---|---|
| CN | 101747361 A | 6/2010 |
| EP | 1942120 A1 | 7/2008 |
| EP | 2045272 A1 | 4/2009 |
| EP | 2338919 A1 | 6/2011 |
| EP | 2484701 A1 | 8/2012 |
| EP | 2647657 A1 | 10/2013 |
| JP | 2008111026 A | 5/2008 |
| JP | 2013060525 A | 4/2013 |
| JP | 2014055264 A | 3/2014 |
| KR | 20080035018 A | 4/2008 |
| KR | 20140126169 A | 10/2014 |
| WO | 2012115769 A2 | 8/2012 |
| WO | 2015057021 A1 | 4/2015 |

OTHER PUBLICATIONS

Extended European Search Report for Application No. 15859197.4 dated Dec. 19, 2016.
International Search Report from PCT/KR2015/011230, dated Feb. 11, 2016.

* cited by examiner

*Primary Examiner* — Marc Zimmer
(74) *Attorney, Agent, or Firm* — Lerner, David, Littenberg, Krumholz & Mentlik, LLP

(57) ABSTRACT

Disclosed are a modified conjugated diene-based polymer represented by specific Chemical Formula and a method of preparing the same.

14 Claims, No Drawings

MODIFIED CONJUGATED DIENE POLYMER, METHOD FOR PREPARING SAME, AND RUBBER COMPOSITION CONTAINING SAME

CROSS-REFERENCE TO RELATED APPLICATION

This application is a national phase entry under 35 U.S.C. §371 of International Application No. PCT/KR2015/011230, filed Oct. 22, 2015, which claims priority to Korean Patent Application No. 10-2014-0158077, filed Nov. 13, 2014 and Korean Patent Application No. 10-2015-0140480, filed Oct. 6, 2015, the disclosures of which are incorporated herein by reference.

TECHNICAL FIELD

The present invention relates to a modified conjugated diene-based polymer, a method of preparing the same, and a rubber composition including the same and, more particularly, to a modified conjugated diene-based polymer having high tensile strength, wear resistance, and wet skid resistance, as well as improved heat build-up when mixed with silica as a reinforcing agent, a method of preparing the same, and a rubber composition including the same.

BACKGROUND ART

The demand for the stability and durability of vehicles is increasing. Accordingly, there is a need to develop rubber having high wet skid resistance and mechanical strength and low rolling resistance, as a material for vehicle tires, especially tire treads, which are in contact with roads.

In conventional tire treads, conjugated diene-based rubber is mixed with an inorganic filler to enhance the above properties, but further enhancement of the properties is still required.

DISCLOSURE

Technical Problem

Therefore, an object of the present invention is to provide a modified conjugated diene-based polymer and a method of preparing the same, in which when a rubber composition includes the modified conjugated diene-based polymer, improved heat build-up and high tensile strength, wear resistance and wet skid resistance may be exhibited.

Another object of the present invention is to provide a modifier for use in preparing the modified conjugated diene-based polymer.

A further object of the present invention is to provide a rubber composition including the modified conjugated diene-based polymer and exhibiting improved heat build-up and high tensile strength, wear resistance and wet skid resistance, and a tire including the rubber composition.

Technical Solution

In order to accomplish the above objects, the present invention provides a modified conjugated diene-based polymer represented by Chemical Formula 1 below:

[Chemical Formula 1]

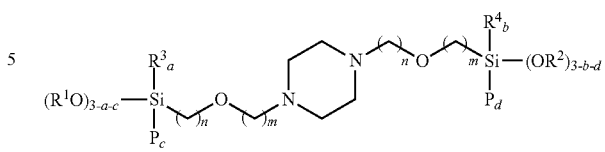

in Chemical Formula 1, $R^1$, $R^2$, $R^3$ and $R^4$ are each independently a C1-C10 alkyl group, P is a conjugated diene-based polymer chain, n and m are each independently from 1 to 10, a and b are each independently 0, 1 or 2, c and d are each independently 0, 1, 2 or 3, both c and d are not 0, and a+c and b+d are each independently 1, 2 or 3.

In addition, the present invention provides a method of preparing a modified conjugated diene-based polymer, comprising: a) polymerizing a conjugated diene monomer or a conjugated diene monomer and an aromatic vinyl monomer using a hydrocarbon solvent in the presence of an organoalkali metal compound, thus forming an active polymer having an alkali metal end; and b) modifying the active polymer having the alkali metal end with a compound represented by Chemical Formula 2 below:

[Chemical Formula 2]

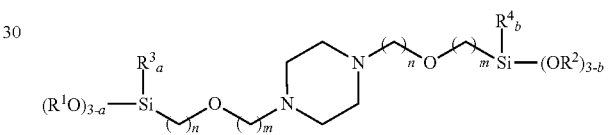

in Chemical Formula 2, $R^1$, $R^2$, $R^3$ and $R^4$ are each independently a C1-C10 alkyl group, n and m are each independently from 1 to 10, and a and b are each independently 0, 1 or 2.

In addition, the present invention provides a modifier represented by Chemical Formula 2 below:

[Chemical Formula 2]

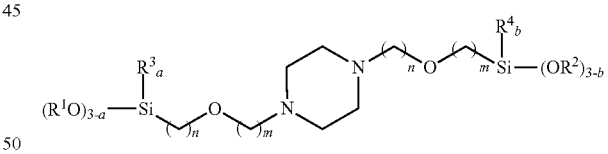

in Chemical Formula 2, $R^1$, $R^2$, $R^3$ and $R^4$ are each independently a C1-C10 alkyl group, n and m are each independently from 1 to 10, and a and b are each independently 0, 1 or 2.

In addition, the present invention provides a modified conjugated diene-based polymer rubber composition, including the modified conjugated diene-based polymer.

In addition, the present invention provides a tire or tire tread, including the modified conjugated diene-based polymer rubber composition.

Advantageous Effects

According to the present invention, a modified conjugated diene-based polymer, which exhibits high tensile strength, wear resistance, and wet skid resistance, as well as improved heat build-up when mixed with silica as a reinforcing agent, can be prepared, and can be utilized to produce a rubber composition for a tire.

BEST MODE

Hereinafter, a detailed description will be given of the present invention.

The present invention addresses a modified conjugated diene-based polymer represented by Chemical Formula 1 below:

[Chemical Formula 1]

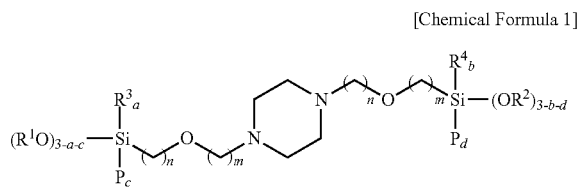

in Chemical Formula 1, $R^1$, $R^2$, $R^3$ and $R^4$ are each independently a C1-C10 alkyl group, P is a conjugated diene-based polymer chain, n and m are each independently from 1 to 10, a and b are each independently 0, 1 or 2, c and d are each independently 0, 1, 2 or 3, both c and d are not 0, and a+c and b+d are each independently 1, 2 or 3.

The conjugated diene-based polymer chain, represented as P in Chemical Formula 1, may be derived from a homopolymer of a conjugated diene monomer or a copolymer of a conjugated diene monomer and a vinyl aromatic monomer.

Specifically, the conjugated diene-based polymer chain may be formed as follows: a conjugated diene monomer, or a conjugated diene monomer and a vinyl aromatic monomer, may be polymerized in a batch manner or a continuous manner using a hydrocarbon solvent in the presence of an organo-alkali metal compound, thus obtaining a homopolymer or a copolymer having an alkali metal end, which is then reacted with a silyl group substituted with at least one alkoxy group.

As such, the conjugated diene-based polymer chain may be a polymer chain comprising the aromatic vinyl monomer in an amount of 0.0001 to 50 wt %, 10 to 40 wt %, or 20 to 40 wt %, based on 100 wt % in total of the conjugated diene monomer, or the conjugated diene monomer and the vinyl aromatic monomer.

The polymer chain comprising the conjugated diene monomer and the vinyl aromatic monomer may be, for example, a random polymer chain.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The vinyl aromatic monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The modified conjugated diene-based polymer may have a Mooney viscosity of 40 or more, preferably from 40 to 90, and more preferably from 50 to 80.

The modified conjugated diene-based polymer may have a number average molecular weight (Mn) of 1,000 to 2,000,000 g/mol, preferably 10,000 to 1,000,000 g/mol, more preferably 100,000 to 1,000,000 g/mol, and most preferably 100,000 to 500,000 g/mol or 200,000 to 700,000 g/mol.

The modified conjugated diene-based polymer has a vinyl content of 18 wt % or more, preferably 25 wt % or more, and more preferably 30 to 70 wt %. Given the above range, the glass transition temperature of the polymer may be elevated. Thus, when such a polymer is applied to tires, the properties required of tires, such as running resistance and braking force, may be satisfied, and superior fuel economy may result.

The vinyl content refers to the amount of a monomer having a vinyl group, or the amount not of 1,4-added conjugated diene monomer but of 1,2-added conjugated diene monomer, based on 100 wt % of the conjugated diene monomer.

The modified conjugated diene-based polymer has a polydispersity index (PDI) of 1 to 10, preferably 1 to 5, and more preferably 1 to 2.

The compound represented by Chemical Formula 1 may be the compound represented by Chemical Formula 1a below:

[Chemical Formula 1a]

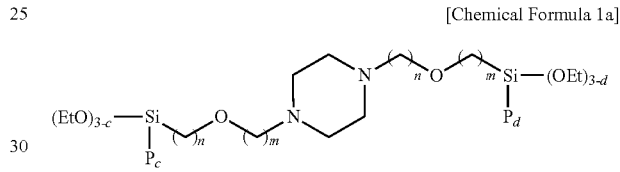

in Chemical Formula 1a, c and d are each independently 0, 1, 2 or 3, both c and d are not 0, and n and m are each independently from 1 to 10.

In addition, the present invention addresses a method of preparing a modified conjugated diene-based polymer, comprising: a) polymerizing a conjugated diene monomer or a conjugated diene monomer and an aromatic vinyl monomer using a hydrocarbon solvent in the presence of an organo-alkali metal compound, thus forming an active polymer having an alkali metal end; and b) modifying the active polymer having the alkali metal end with a compound represented by Chemical Formula 2 below:

[Chemical Formula 2]

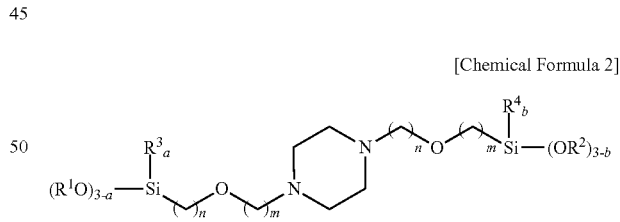

in Chemical Formula 2, $R^1$, $R^2$, $R^3$ and $R^4$ are each independently a C1-C10 alkyl group, n and m are each independently from 1 to 10, and a and b are each independently 0, 1 or 2.

The organo-alkali metal compound may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferably useful as the organo-alkali metal compound is n-butyllithium, sec-butyllithium or a mixture thereof.

Alternatively, the organo-alkali metal compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with another organo-alkali metal compound.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Preferably useful is styrene or α-methylstyrene.

In an embodiment of the present invention, the organo-alkali metal compound may be used in an amount of 0.01 to 10 mmol, 0.05 to 5 mmol, 0.1 to 2 mmol, or 0.1 to 1 mmol, relative to the molar ratio for activation, based on 100 g in total of the monomer. The expression 'relative to the molar ratio for activation' means the amount used for activation because the organo-alkali metal compound of the present invention may be inactivated depending on the water content. When the amount of the organo-alkali metal compound falls in the above range, a conjugated diene-based polymer optimal for use in the preparation of a modified conjugated diene-based polymer may be obtained.

The molar ratio of the organo-alkali metal compound and the compound represented by Chemical Formula 2 may be, for example, 1:0.1 to 1:10, and preferably 1:0.3 to 1:2. When the molar ratio thereof falls in the above range, the conjugated diene-based polymer may be subjected to a modification reaction to ensure optimal performance.

As used herein, the active polymer having an alkali metal end refers to a polymer comprising a polymer anion and an alkali metal cation, which are coupled with each other.

In the method of preparing the modified conjugated diene-based polymer according to an embodiment of the present invention, the polymerizing in a) may be performed with the additional use of a polar additive. The reason why the polar additive is further added is that the reaction rates of the conjugated diene monomer and the aromatic vinyl monomer are controlled by the polar additive.

The polar additive may be a base, or may include ether, amine or mixtures thereof. Specifically, it may be selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine. Preferably useful is ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

The polar additive may be used in an amount of 0.001 to 10 g, 0.005 to 1 g, or 0.005 to 0.1 g, based on 1 mmol in total of the added organo-alkali metal compound.

When the conjugated diene monomer and the aromatic vinyl monomer are copolymerized, a block copolymer may be readily prepared due to the difference in the reaction rates therebetween. However, when the polar additive is added, the low reaction rate of the aromatic vinyl monomer may be increased to thus obtain the microstructure of the corresponding copolymer, for example, a random copolymer.

In a), the polymerization may be exemplified by anionic polymerization. Specifically, the polymerization in a) may be living anionic polymerization in which an active end is obtained through a growth reaction involving anions.

Also, the polymerization in a) may be either high-temperature polymerization or room-temperature polymerization.

High-temperature polymerization is a polymerization process that comprises adding the organometallic compound and then applying heat to increase the reaction temperature, and room-temperature polymerization is a polymerization process that takes place in such a way that heat is not applied after the organometallic compound is added.

The polymerization in a) may take place at a temperature ranging from −20 to 200° C., 0 to 150° C., or 10 to 120° C.

In b) according to the method of the invention, the active polymer having the alkali metal end is modified with the compound represented by Chemical Formula 2 below:

[Chemical Formula 2]

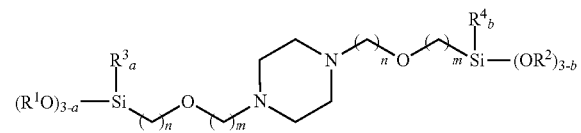

in Chemical Formula 2, $R^1$, $R^2$, $R^3$ and $R^4$ are each independently a C1-C10 alkyl group, n and m are each independently from 1 to 10, and a and b are each independently 0, 1 or 2.

The compound represented by Chemical Formula 2 may be the compound represented by Chemical Formula 2a below:

[Chemical Formula 2a]

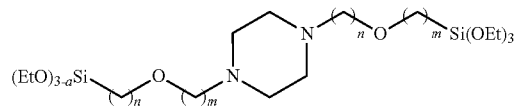

in Chemical Formula 2a, n and m are each independently from 1 to 10.

In b), at least one, or two or three, selected from among compounds represented by Chemical Formula 1, may be added.

Also, (b) may be carried out at 0 to 90° C. for 1 min to 5 hr.

The method of preparing the modified conjugated diene-based polymer according to an embodiment of the present invention may be carried out in a batch manner, or alternatively in a continuous manner using at least one reactor.

In addition, the present invention addresses a modifier, which is a compound represented by Chemical Formula 2 below:

[Chemical Formula 2]

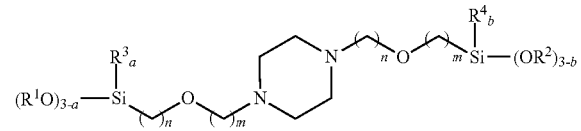

in Chemical Formula 2, $R^1$, $R^2$, $R^3$ and $R^4$ are each independently a C1-C10 alkyl group, n and m are each independently from 1 to 10, and a and b are each independently 0, 1 or 2.

The compound represented by Chemical Formula 2 may be the compound represented by Chemical Formula 2a below:

[Chemical Formula 2a]

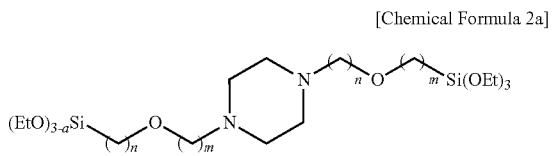

in Chemical Formula 2a, n and m are each independently from 1 to 10.

In addition, the present invention addresses a modified conjugated diene-based polymer rubber composition, comprising 10 to 100 parts by weight of the modified conjugated diene-based polymer and 0.1 to 200 parts by weight of an inorganic filler based on 100 parts by weight of the modified conjugated diene-based polymer.

The amount of the inorganic filler may be 10 to 150 parts by weight, or 50 to 100 parts by weight.

The inorganic filler may include at least one selected from the group consisting of a silica-based filler, carbon black, and mixtures thereof. When the inorganic filler is a silica-based filler, dispersibility is significantly increased and the end of the modified conjugated diene-based polymer of the invention may be coupled with silica particles, thus significantly decreasing hysteresis loss.

The modified conjugated diene-based polymer rubber composition may further comprise an additional conjugated diene-based polymer.

The additional conjugated diene-based polymer may include SBR (styrene-butadiene rubber), BR (butadiene rubber), natural rubber, or mixtures thereof. SBR may be exemplified by SSBR (solution styrene-butadiene rubber).

When the additional conjugated diene-based polymer is further added, the modified conjugated diene-based polymer rubber composition may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

In addition, the modified conjugated diene-based polymer rubber composition may further comprise 1 to 100 parts by weight of oil. The oil may be exemplified by mineral oil or a softener.

The oil may be used in an amount of, for example, 10 to 100 parts by weight, or 20 to 80 parts by weight, based on 100 parts by weight of the conjugated diene-based polymer. Given the above range, the rubber composition may exhibit desired properties, and may be appropriately softened, thus increasing processability.

The modified conjugated diene-based polymer may have a Mooney viscosity of 40 or more, preferably from 40 to 100, and more preferably from 45 to 90. When the Mooney viscosity thereof falls in the above range, a modified conjugated diene-based polymer having improved heat build-up and high processability, compatibility, tensile strength, wear resistance, fuel economy, and wet skid resistance may be prepared.

The modified conjugated diene-based polymer may exhibit viscoelastic properties. When measured at 10 Hz using DMA after mixing with silica, Tan δ at 0° C. may be in the range of 0.4 to 1, or 0.5 to 1. Given the above Tan δ range, desired skid resistance or wet resistance may be obtained.

Also, Tan δ at 60° C. may be in the range of 0.3 to 0.2, or 0.15 to 0.1. Given the above Tan δ range, desired rolling resistance or rotational resistance (RR) may be obtained.

In addition, the present invention addresses a tire or tire tread using the modified conjugated diene-based polymer rubber composition described above.

The tire or tire tread is manufactured using the rubber composition comprising the modified conjugated diene-based polymer, which has high processability and superior compatibility with the inorganic filler, and thereby can manifest improved heat build-up and high tensile strength, wear resistance, and wet skid resistance, as well as low rolling resistance.

MODE FOR INVENTION

A better understanding of the present invention may be obtained via the following examples. However, the examples of the present invention may be changed in various forms, and are not construed as limiting the scope of the present invention. The examples of the present invention are provided to fully describe the present invention to those having ordinary knowledge in the art to which the present invention pertains.

EXAMPLE 1

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 2.5 g of n-butyllithium was placed in the reactor, followed by an adiabatic heating reaction. After about 20 min, 20 g of 1,3-butadiene was added. After 5 min, 0.7 g of 1,4-bis(3-(3-(triethoxysilyl)propoxy)propyl)piperazine was added, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

EXAMPLE 2

A sample was prepared in the same manner as in Example 1, with the exception that 1.5 g of 1,4-bis(3-(3-(triethoxysilyl)propoxy)propyl)piperazine was added.

EXAMPLE 3

A sample was prepared in the same manner as in Example 1, with the exception that 2 g of 1,4-bis(3-(3-(triethoxysilyl)propoxy)propyl)piperazine was added.

COMPARATIVE EXAMPLE 1

A sample was prepared in the same manner as in Example 1, with the exception that 1,4-bis(3-(3-(triethoxysilyl)propoxy)propyl)piperazine was not added.

COMPARATIVE EXAMPLE 2

A sample was prepared in the same manner as in Example 1, with the exception that 1.8 g of 1,4-bis(3-(triethoxysilyl)propyl)piperazine was added.

The conjugated diene-based polymers of Examples 1 to 3 and Comparative Examples 1 and 2 were analyzed through the following methods.

a) Mooney viscosity: two samples having a weight of 15 g or more were preheated for 1 min and then measured at 100° C. for 4 min using an MV-2000, made by ALPHA Technologies.

b) Styrene monomer (SM) and Vinyl content: measurement was conducted using NMR.

c) Weight average molecular weight (Mw), Number average molecular weight (Mn), and Polydispersity Index (PDI): measurement was conducted via GPC at 40° C. The column herein used was a combination of two PLgel Olexis columns and one PLgel mixed-C column, made by Polymer Laboratories, and all of the replaced columns were mixed bed-type columns. Also, polystyrene (PS) was the GPC standard material for the calculation of molecular weight.

TABLE 1

|  |  | Ex. 1 | Ex. 2 | Ex. 3 | C. Ex. 1 | C. Ex. 2 |
| --- | --- | --- | --- | --- | --- | --- |
| Sample |  | A | B | C | D | E |
| Modifier |  |  | a |  | — | b |
| Modifier equivalent eq/[NBL] |  | 0.5 | 1.0 | 1.5 | — | 1.5 |
| Mooney |  | 78 | 70 | 69 | 63 | 68 |
| Styrene (%) |  | 26 | 27 | 27 | 27 | 26 |
| Vinyl (%) |  | 42 | 41 | 42 | 41 | 41 |
| GPC (×10$^4$) | Mn | 40 | 38 | 36 | 34 | 37 |
|  | Mw | 62 | 58 | 50 | 41 | 50 |
|  | PDI | 1.6 | 1.5 | 1.4 | 1.2 | 1.3 | a: 1,4-bis(3-(3-(triethoxysilyl)propoxy)propyl)piperazine
b: 1,4-bis(3-(triethoxysilyl)propyl)piperazine The conjugated diene-based polymer rubber compositions were prepared using, as raw rubber, samples A to E, shown in Table 1, under the mixing conditions of Table 2 below. The unit of material in Table 2 is phr, based on 100 parts by weight of rubber.

Specifically, the conjugated diene-based polymer rubber composition was kneaded through primary kneading and secondary kneading. Upon primary kneading, raw rubber (conjugated diene-based polymer), a filler, an organosilane coupling agent, oil, zinc oxide, a stearic acid antioxidant, an anti-aging agent, wax and an accelerator were kneaded using a Banbury mixer provided with a temperature controller. For this, the temperature of the kneader was controlled, and a first mixture was obtained at a discharge temperature of 145 to 155° C. Upon secondary kneading, the first mixture was cooled to room temperature, after which rubber, sulfur and a vulcanization accelerator were placed in the kneader, followed by mixing at 100° C. or less, thus obtaining a second mixture. Finally, curing was performed at 100° C. for 20 min, yielding the conjugated diene-based polymer rubber compositions of Preparation Examples 1 to 3 using, as raw rubber, the polymers of Examples 1 to 3, and of Comparative Preparation Examples 1 and 2 using the polymers of Comparative Examples 1 and 2 as raw rubber.

TABLE 2

|  | Material | Amount (unit: phr) |
| --- | --- | --- |
| Primary kneading | Rubber | 100 |
|  | Silica | 70.0 |
|  | Coupling agent | 11.2 |
|  | Oil | 37.5 |
|  | Zinc oxide | 3.0 |
|  | Stearic acid | 2.0 |
|  | Antioxidant | 2.0 |
|  | Anti-aging agent | 2.0 |
|  | Wax | 1.0 |
| Secondary kneading | Rubber accelerator | 1.75 |
|  | Sulfur | 1.5 |
|  | Vulcanization accelerator | 2.0 |
|  | Total weight | 233.95 |

The properties of the prepared rubber compositions were measured through the following methods.

1) Tensile Testing

According to the tensile testing method of ASTM 412, the tensile strength upon cutting a test sample and tensile stress (300% modulus) at 300% elongation were measured. For this, the tensile strength, modulus, and elongation were measured at a tensile speed of 50 cm/min at room temperature using, as a tensile tester, a Universal Test Machine 4204, made by Instron.

2) Viscoelasticity

A dynamic mechanical analyzer made by TA was used. When undergoing deformation under conditions of a frequency of 10 Hz in a distortion mode and a measurement temperature (ranging from −60 to 60° C.), the Tan δ of each sample was measured. The Payne effect was represented by the difference between the minimum and the maximum in the deformation range of 0.28 to 40%. The lower the Payne effect, the higher the dispersibility of the filler such as silica. When Tan δ at 0° C., which is a low temperature, was increased, wet skid resistance became superior, and when Tan δ at 60° C., which is a high temperature, was decreased, hysteresis loss was reduced, resulting in low rolling resistance of tires, and thus superior fuel economy. Table 3 below shows the properties of the vulcanized rubber.

TABLE 3

|  | Test Ex. 1 | Test Ex. 2 | Test Ex. 3 | C. Test Ex. 1 | C. Test Ex. 2 |
|---|---|---|---|---|---|
| Sample | A | B | C | D | E |
| 300% Modulus (Kgf/cm$^2$) | 110 | 118 | 119 | 95 | 115 |
| Tensile strength (Kgf/cm$^2$) | 183 | 185 | 181 | 192 | 168 |
| Tanδ at 0° C. | 114 | 118 | 119 | 100 | 115 |
| Tanδ at 60° C. | 117 | 118 | 120 | 100 | 118 |

As is apparent from the results of Table 3, compared to Comparative Preparation Examples 1 and 2, the modified conjugated diene-based polymer rubber compositions of Preparation Examples 1 to 3 according to the present invention were significantly increased in 300% modulus (tensile stress) and tensile strength, and also exhibited low Tan δ at 60° C. Thus, when the modified conjugated diene-based polymer rubber composition according to the present invention was used in a tire, rolling resistance was decreased, whereby superior fuel efficiency resulted.

Also, the conjugated diene-based polymer rubber compositions of Preparation Examples 1 to 3 according to the present invention exhibited high Tan δ at 0° C., compared to Comparative Preparation Example 2. Thus, when the modified conjugated diene-based polymer rubber composition of the invention was used in a tire, high wet skid resistance resulted.

The invention claimed is:

1. A modified conjugated diene-based polymer represented by Chemical Formula 1 below:

[Chemical Formula 1]

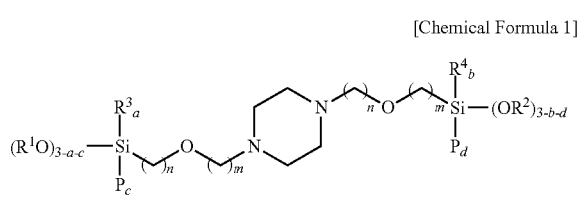

in Chemical Formula 1, R$^1$, R$^2$, R$^3$ and R$^4$ are each independently a C1-C10 alkyl group, P is a conjugated diene-based polymer chain, n and m are each independently from 1 to 10, a and b are each independently 0, 1 or 2, c and d are each independently 0, 1, 2 or 3, both c and d are not 0, and a+c and b+d are each independently 1, 2 or 3.

2. A modified conjugated diene-based polymer represented by Chemical Formula 1a below:

[Chemical Formula 1a]

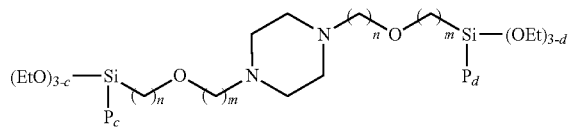

in Chemical Formula 1a, c and d are each independently 0, 1, 2 or 3, both c and d are not 0, and n and m are each independently from 1 to 10.

3. The modified conjugated diene-based polymer of claim 1, wherein the modified conjugated diene-based polymer has a number average molecular weight (Mn) of 1,000 to 2,000,000 g/mol.

4. A method of preparing a modified conjugated diene-based polymer, comprising:
  a) polymerizing a conjugated diene monomer or a conjugated diene monomer and an aromatic vinyl monomer using a hydrocarbon solvent in presence of an organo-alkali metal compound, thus forming an active polymer having an alkali metal end; and
  b) modifying the active polymer having the alkali metal end with a compound represented by Chemical Formula 2 below:

[Chemical Formula 2]

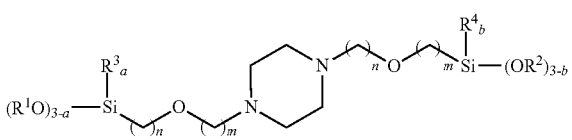

in Chemical Formula 2, R$^1$, R$^2$, R$^3$ and R$^4$ are each independently a C1-C10 alkyl group, n and m are each independently from 1 to 10, and a and b are each independently 0, 1 or 2.

5. The method of claim 4, wherein the compound represented by Chemical Formula 2 is a compound represented by Chemical Formula 2a below:

[Chemical Formula 2a]

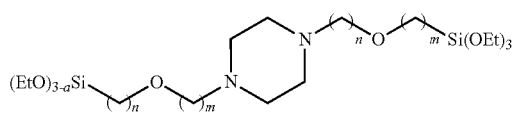

in Chemical Formula 2a, n and m are each independently from 1 to 10.

6. The method of claim 4, wherein the organo-alkali metal compound is used in an amount of 0.01 to 10 mmol, relative to a molar ratio for activation, based on 100 g in total of the monomer.

7. The method of claim 4, wherein a molar ratio of the organo-alkali metal compound and the compound represented by Chemical Formula 2 is 1:0.1 to 1:10.

8. The method of claim 4, wherein the polymerizing in a) is performed with additional use of a polar additive.

9. The method of claim 8, wherein the polar additive is added in an amount of 0.001 to 10 g based on 1 mmol in total of the organo-alkali metal compound.

10. A modifier, which is a compound represented by Chemical Formula 2 below:

[Chemical Formula 2]

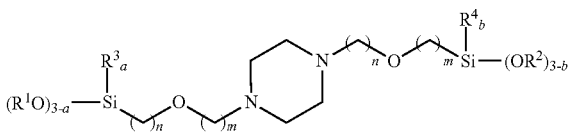

in Chemical Formula 2, R$^1$, R$^2$, R$^3$ and R$^4$ are each independently a C1-C10 alkyl group, n and m are each independently from 1 to 10, and a and b are each independently 0, 1 or 2.

11. The modifier of claim 10, wherein the compound represented by Chemical Formula 2 is a compound represented by Chemical Formula 2a below:

[Chemical Formula 2a]

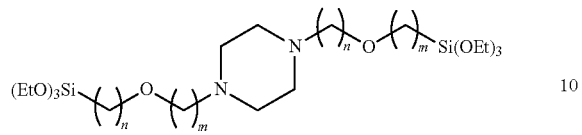

in Chemical Formula 2a, n and m are each independently from 1 to 10.

12. A modified conjugated diene-based polymer rubber composition, comprising 10 to 100 parts by weight of the modified conjugated diene-based polymer of claim 1 and 0.1 to 200 parts by weight of an inorganic filler based on 100 parts by weight of the modified conjugated diene-based polymer.

13. The modified conjugated diene-based polymer rubber composition of claim 12, wherein the inorganic filler comprises at least one selected from the group consisting of a silica-based filler, carbon black, and mixtures thereof.

14. A tire or tire tread, comprising the modified conjugated diene-based polymer rubber composition of claim 12.

* * * * *